(12) United States Patent
Gupta

(10) Patent No.: US 10,575,789 B2
(45) Date of Patent: Mar. 3, 2020

(54) RANDOM FOREST BASED ERYTHEMA GRADING FOR PSORIASIS

(71) Applicant: RICOH CO., LTD., Tokjo OT (JP)

(72) Inventor: Mithun Das Gupta, Menlo Park, CA (US)

(73) Assignee: RICOH CO., LTD., Tokyo (JP)

( * ) Notice: Subject to any disclaimer, the term of this patent is extended or adjusted under 35 U.S.C. 154(b) by 1183 days.

(21) Appl. No.: 14/562,206

(22) Filed: Dec. 5, 2014

(65) Prior Publication Data
US 2016/0157786 A1    Jun. 9, 2016

(51) Int. Cl.
    *A61B 5/00*     (2006.01)
(52) U.S. Cl.
    CPC .......... *A61B 5/7264* (2013.01); *A61B 5/0075* (2013.01); *A61B 5/445* (2013.01)
(58) Field of Classification Search
    CPC .................................................... A61B 5/445
    See application file for complete search history.

(56) References Cited

U.S. PATENT DOCUMENTS

| 2006/0269111 A1* | 11/2006 | Stoecker | G06F 19/321 382/128 |
| 2009/0318815 A1* | 12/2009 | Barnes | A61B 5/0062 600/473 |

FOREIGN PATENT DOCUMENTS

WO     2000041714     6/2002

OTHER PUBLICATIONS

Indian Office Action for Application No. 3923/DEL/2015, dated Aug. 27, 2019, 6 pages.

* cited by examiner

*Primary Examiner* — Jacqueline Cheng
*Assistant Examiner* — Tho Q Tran
(74) *Attorney, Agent, or Firm* — Womble Bond Dickinson (US) LLP

(57) ABSTRACT

A method and apparatus is disclosed herein for erythema grading for psoriasis. In one embodiment, the method comprises generating Skellam distribution statistics related to differences between readout voltages for one or more psoriasis regions for a patient and a normal skin region for the patient; and generating an erythema grading classification for erythema regions in psoriasis using the Skellam distribution statistics as feature vectors.

18 Claims, 5 Drawing Sheets

RANDOM FOREST BASED ERYTHEMA GRADING FOR PSORIASIS

FIELD OF THE INVENTION

Embodiments of the present invention relate to the field of erythema grading for psoriasis; more particularly, embodiments of the present invention relate to erythema grading for psoriasis that is skin tone independent.

BACKGROUND OF THE INVENTION

Psoriasis is a systemic, immunological, genetic disease manifesting in the skin and/or joints. Because of its systemic nature, patients exhibit a broad spectrum of symptoms that vary in severity. Psoriasis is a lifelong, chronic, recurrent disease. In patient surveys conducted between 2001 and 2008 by the National Psoriasis Foundation, 33% of patients with mild disease and 60% of patients with moderate-to-severe reported that their disease was a significant problem in their everyday life. The severity score is a number that is used to classify the severity of psoriasis. A widely used severity score is the Psoriasis Area and Severity Index, or PASI score. The PASI score is calculated by dividing the body into a number of regions and grading the severity of the erythema (the red inflamed skin), and the severity of the scaling (the scaly, flaky skin typically found inside a lesion) within a region. That is, erythema or redness of skin is an important identifier for evaluation of the PASI score. The severity of erythema and scaling in PASI scores are estimated visually often leading to significant inter- and intra-individual variation in scores. Extra subjectiveness in the evaluation of erythema has been observed, since the perception of redness can be influenced by the skin tone, ambient lighting and many other such factors which are difficult to control in a clinical setting. Further, PAST scores require that the symptoms of several lesions are estimated which greatly increases the workload of dermatologists.

Computer aided methods for psoriasis severity scoring have been under investigation for a number of decades. In at least one technique, the severity scores for erythema are correlated with the hue (H) value and saturation (S) value in the HSV color model. The color differences between psoriasis lesions and normal skin were previously investigated, and the investigation concluded that the distribution of erythema severity is correlated with the difference in hue value. However, in that investigation, the color value is sampled randomly while ignoring the variation in lesion and skin color to assess psoriasis severity. In yet another technique, the colors of pigments in lesions are used to derive mean color values in RGB colors space and then these are used to grade the severity of lesions using K-Nearest Neighbors.

SUMMARY OF THE INVENTION

A method and apparatus is disclosed herein for erythema grading for psoriasis. In one embodiment, the method comprises generating Skellam distribution statistics related to differences between readout voltages for one or more psoriasis regions for a patient and a normal skin region for the patient; and generating an erythema grading classification for erythema regions in psoriasis using the Skellam distribution statistics as feature vectors.

Embodiments of the present invention can take other forms such as other systems, methods, articles of manufacture, and computer readable storage media.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PRESENT INVENTION

Figure 1:
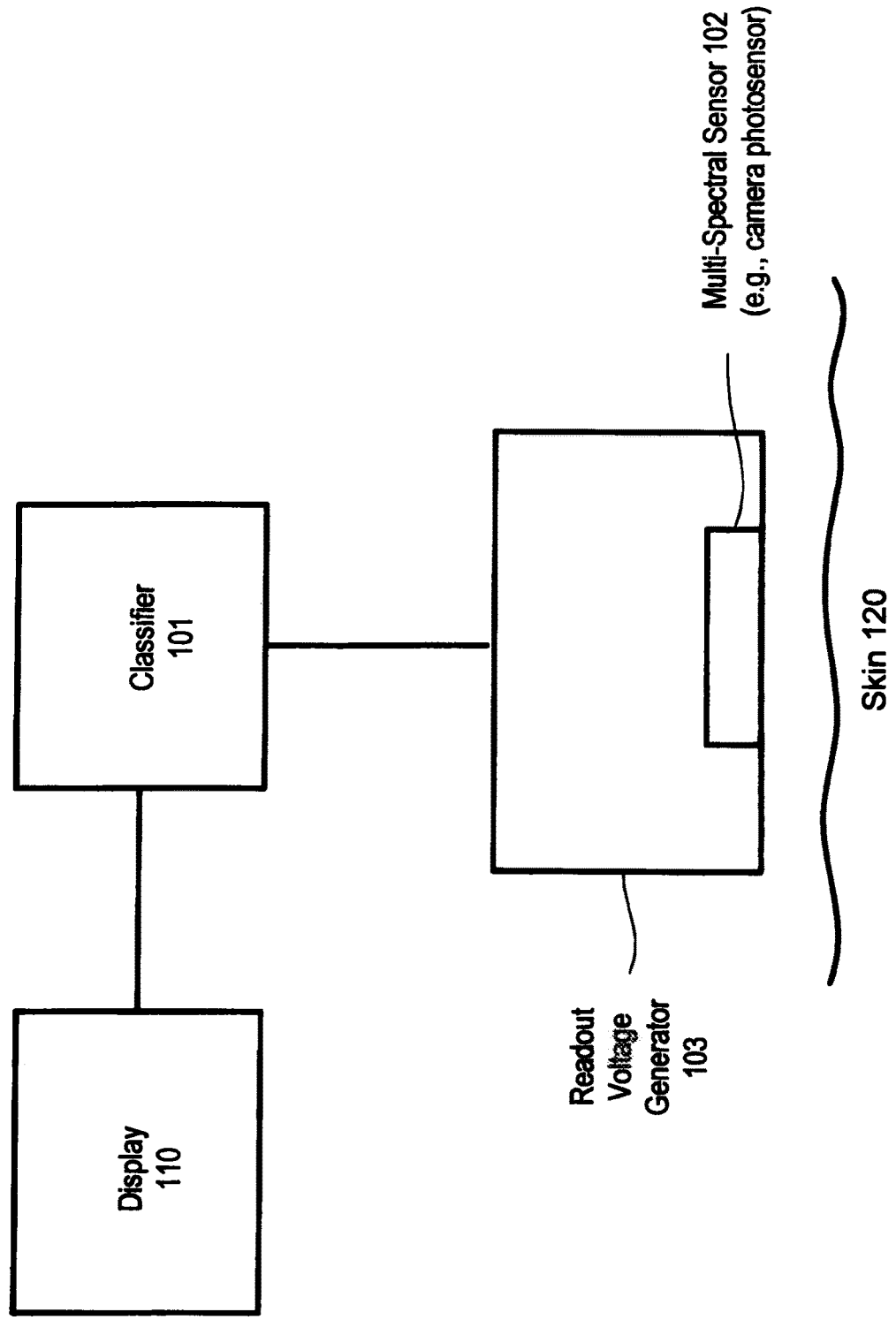
FIG. 1 is a block diagram of one embodiment of an apparatus for erythema grading.

A method and apparatus for erythema grading for psoriasis are described. The erythema grading uses a tissue-photon interaction model that allows the grading to be skin tone independent. The techniques described herein provide an automatic scoring method that greatly helps reduce variation in scoring due to a reduction, and possibly an elimination, of estimations done by clinicians, thus reducing (or eliminating) variations in estimations which are influenced by perceptions of redness influenced by skin tone, ambient lighting, etc. This helps to improve treatment research and clinical outcomes for patients as well as reducing the workload for clinicians. In one embodiment, the techniques use Skellam distribution statistics as feature vectors for erythema grading. A random forest based technique uses these feature vectors as input and outputs classification categories to indicate a classification of erythema regions in psoriasis.

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a non-transitory computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; etc.

Overview

A technique for automatically estimating the severity of erythema using multi-spectral digital skin images is disclosed. The estimate may be used to compute a PASI score. Techniques described herein derive a series of features that relate to the redness of erythema and are based on a haemoglobin and melanin color space and the relative scaling area and texture. Haemoglobin is related to the red color in skin and melanin is related to the yellow and brown color in skin.

FIG. 1 is a block diagram of one embodiment of a erythema grading system. Referring to FIG. 1, a multi-spectral sensor 102 includes server elements that record photons that are reflected off skin surface 120 in response to a light source (not shown). Sensor 102 includes a plurality of filters selective to photons around respective central wavelengths. In one embodiment, sensor 102 has eight optical band-pass filters. In one embodiment, the different wavelength spectrum used for imaging include one or more of the following: 3 wideband (100 nm) filters centered at 445=(blue), 550 nm (green) and 650 nm (red) and 5 narrowband (10 nm) filters centered at 542 nm, 680 nm, 750 nm, 800 nm, and 860 nm. Thus, sensor 102 includes filters for the RGB wideband channels.

A readout voltage generator 103 measures the number of photons for the photons that are incident of the sensor elements through the filters and generates readout voltages indicative of incident photons. Readout voltage generator 103 sends those voltages to classifier 101.

In one embodiment, sensor 102 and readout voltage generator 103 are part of a camera, such as, for example, a multi-spectral camera.

In response to the readout voltages, classifier 101 performs erythema grading for psoriasis. In one embodiment, this is performed automatically using a tissue-photon interaction model that makes the erythema grading skin tone independent. In one embodiment, feature vectors used for erythema grading include Skellam distribution statistics. In one embodiment, classifier 101 inputs those feature vectors into a random forest-based technique to classify erythema regions into psoriasis categories, such as, for example, severe, moderate, and slight. Classifier 101 outputs the category to an output device, such as display 110.

Tissue Photon Interaction Model

The erythema grading system illuminates (with an illumination source) a skin region and the number of photons reflected are sensed and recorded using a sensor. In one embodiment, the sensor is a photosensor. The rate of photon induced electron generation ($\rho$) at a site on the camera photo-sensor can defined as $$\rho = \int_\lambda \int_y \int_x B(x,y,\lambda) S_r(x,y) q(\kappa) dx dy d\lambda \qquad (1)$$

where (x,y) are continuous coordinates on the sensor plane, $q(\lambda)$ is the internal quantum efficiency of the detector (electrons/Joule) as a function of wavelength of incident radiation ($\lambda$). $S_r(x,y)$ is the spatial response of the collection site on the sensor. The spectral irradiance pattern $B(x,y,\lambda)$ (Watts/unit area) incident on the sensor is modelled as $$B(x,y,\lambda) = \{R(x,y,\lambda)L(x,y,\lambda)*p(x,y,\lambda)\}t(\lambda) \qquad (2)$$

where * is the spatial convolution operator, $p(x,y,\lambda)$ is the point-spread-function of the camera lens system, and $t(\lambda)$ is the spectral transmission of the optics. $R(x,y,\lambda)$ is the spatially varying spectral reflectance of the surface being imaged, and $L(x,y,\lambda)$ is the spatially varying illumination model.

The photon induced voltage (D) sensed and subsequently read out of the sensor circuitry is given by $$D(K\rho T + N_{DC} + N_S + N_R)A + N_Q,$$

where K is the external quantum efficiency of the sensor (Volts/electron), T is the typical integration time of the sensor, $N_{DC}$ is the dark current noise, $N_S$ is the shot noise, $N_R$ is the readout noise, A is the amplification factor of the readout circuitry, $N_Q$ is the quantization noise of the ADC. In pre-calibrated sensors, $N_{DC}, N_S, N_R, N_Q \ll K\rho T$, ensuring that $D \approx AK\rho T = \rho T_1$ in normal operating conditions.

$S_r(x,y)$, and $q(\lambda)$ in Eq. 1 remain constant for a sensor and vary only with change of sensors. $p(x,y,\lambda), t(\lambda),$ and $L(x,y,\lambda)$ in Eq. 2 remain constant if the camera optics and illumination source are kept unchanged. Consequently, the only variable factor is $R(x,y,\lambda)$ in Eq. 2 and it is indicative of photon-tissue interaction.

The digitally readout voltage (d) from a sensor is a stochastically sensed value of the induced voltage (D) at an instance and is known to be Poisson distributed with $$Pr(D=d) \propto \frac{(\rho \overline{T})^d e^{-\rho T}}{d!} \lambda \in [\lambda_1, \lambda_2] \qquad (3)$$

where $\rho\bar{T}=AK\rho T=E[d]=var(d)$, with $E[\cdot]$ and $var(\cdot)$ representing mathematical expectation and variance operators, respectively. $[\lambda_1, \lambda_2]$ is the range of optical radiation wavelength to which the system is responsive. That is, $\rho\bar{T}$ is equal to both the mathematical expectation of the digitally readout voltage d and the variance of the digitally readout voltage d. In one embodiment, the multi-spectral sensor has eight optical band-pass filters selective to photons around the respective central wavelengths. Thus, the rate of photon incidence on the sensor elements are $\rho_\lambda$ for each of the filters. Each of these measurements follow the Poisson distribution as indicated in Eq. 3 for the readings for the particular wavelength. The parameters defining this distribution can be estimated locally as $\rho_\lambda T=E[d_\lambda]$. For a given camera and lighting configuration, $\rho_\lambda T$ is proportional to $R(x,y,\lambda)$ and for known sensor integration time T, it is used to model the photon-tissue interaction.

In one embodiment, $\rho_A T$ at a location $(x,y)\in I$ is estimated using samples in a neighborhood of size $n_1 \times n_2$ pixel centered at $(x,y)$. The fidelity of estimation is dependent on the number of samples used. In one embodiment, $\rho_\lambda T$ is estimated at multiple neighborhood sizes represented by scale k, such that $p_\lambda^k \bar{T}=E[d_\lambda^k]$ is the estimation for wavelength $\lambda$ using samples at scale k. Examples of sizes of n1 and n2 are n1=n2=3, 5, 7. Other sizes may be used, and n1 and n2 need not be the same size. Samples are collected over multiple scales and all wavelength channels to generate the following feature vector $$\Phi_{x,y}=\{E[d_\lambda^k]\}, \lambda\in[\lambda_1,\lambda_2], k\in[1, \ldots, K].$$

Skin Tone Independent Tissue-Photon Characteristics

One of the primary necessities of the erythema grading system is to make it agnostic to the base skin color of the patient because erythema looks more prominent in fairer persons than their darker counterparts. The readout voltage (image intensity) for a particular wavelength at an affected site (a skin region suspected of having psoriasis) is $d_e$. This is known to be a Poisson distributed random variable $p(d_e; \rho_\lambda T)$. The readout voltage $d_{ns}$, for the normal skin region for the same patient is subtracted from $d_e$. Then, the difference term $d_d = d_e - d_{ns}$ is now distributed as a Skellam distribution given by $$f(k; \rho_1 \bar{T}_1, \rho_2 \bar{T}_2) = e^{-(\rho_1 \bar{T}_1 + \rho_2 \bar{T}_2)}\left(\frac{\rho_1 \bar{T}_1}{\rho_2 \bar{T}_2}\right)^{k/2} I_k\left(2\sqrt{\rho_1 \bar{T}_1 \rho_2 \bar{T}_2}\right) \quad (4)$$

where $I_k(z)$ is the modified Bessel function of the first kind. The difference voltage $d_d$ is substituted for "k" in equation above (except for the last term $I_k$ which is a standard term). The mean $\mu_S$ and the variance $\sigma_S^2$ for the Skellam distribution can be obtained as $$\mu_S = \rho_1 \bar{T}_1 - \rho_2 \bar{T}_2 \quad (5)$$

$$\sigma_S^2 = \rho_1 \bar{T}_1 + \rho_2 \bar{T}_2 \quad (6)$$

Skellam Distribution Parameter Estimation

Consequently, the estimate for the skin tone independent tissue photon characteristics (at different scales) becomes $$\bar{\Phi}_{x,y} = \bar{\mu}_S \approx \{E[d_e^{k\lambda}] - E[d_{ns}^\lambda]\} \lambda \in [\lambda_1, \lambda_2], k\in[1, \ldots, K] \quad (7)$$

where $\bar{\mu}_S$ is an estimate for the true mean $\mu_S$. Note that $E[d_{ns}^\lambda]$ is independent of location. In one embodiment, the E is computed once per patient for the normal skin region in the captured image.

Random Forests for Erythema Grading

Given the assumption that photon interaction statistical physics is tissue specific, $R(x,y,\lambda)$ in Eq. 2 would be specific for the three groups of erythema $\omega \in \{$slight, moderate, severe$\}$ as graded by dermatologists. The feature vector $\bar{\Phi}$ in Eq. 7 forms an erythema specific set of observations $\{\bar{\Phi}\}|\omega$ that can be learned using a set of training samples $\{I\}$train. The set of observations $\{\bar{\Phi}\}|\omega$ generally forms non-parametric distributed clusters and learning of such spaces is efficiently achieved using supervised non-parametric learners such as random forests. Other examples of non-parametric learners that could be used are decision forests, etc.

In one embodiment, a random forest non-parametric supervised learner is used to learn this set $\{\bar{\Phi}\}|\omega$ as the model $H(\omega|\bar{\Phi}, I; \{I\}$train) in a manner well-known to those skilled in the art. A random forest is an ensemble of multiple decision trees $h_n(\cdot)$ that jointly form the model $H(\cdot)$. In one embodiment, each tree is a binary decision tree. The present invention is not limited to using binary decision trees and be any other configuration.

The observation space is generally bootstrapped to learn the trees in a de-correlated fashion. In one embodiment, each tree consists of an ordered network of nodes, either decision making nodes or leaf nodes. The response of a tree is the information yield from a leaf node, e.g. posterior probability of a class $\omega$ based on observations $\bar{\Phi}$. The decision of the forest can be aggregated using bagging of decisions from each tree. In a binary tree, the decision making nodes select a split to subsequently push an observation to its left or right child. This split is made using a splitting criteria generally formulated from a subset of randomly chosen feature subset. Each tree can be learned up to a maximum depth or until the number of observations arriving at each node is more than a certain threshold. The response of the learned forest $H(\omega|\bar{\Phi}, I; \{I\}$train) is probability p $(\omega|I, (x,y))$ of grading a pixel at $(x,y)$ on the image I.

For each patient, a reference normal skin region is also chosen. Patch-mean features are learned for every pixel from the erythema region and the normal skin region. The features for all the pixels from the normal skin region are averaged to generate the normalized base skin feature for the particular patient. This normalized base skin feature is then subtracted from the erythema region pixel features to generate the final set of features for classification.

In one embodiment, when testing on individual patients, each patient is imaged at more than one site, candidate regions from each site are generated and a site specific category. e.g., for patient x, for site 1 let the inferred category be slight, for site 2 is inferred. In one embodiment, rating for patient x to be moderate based on the worst rating category inferred over all sites.

Figure 2A:
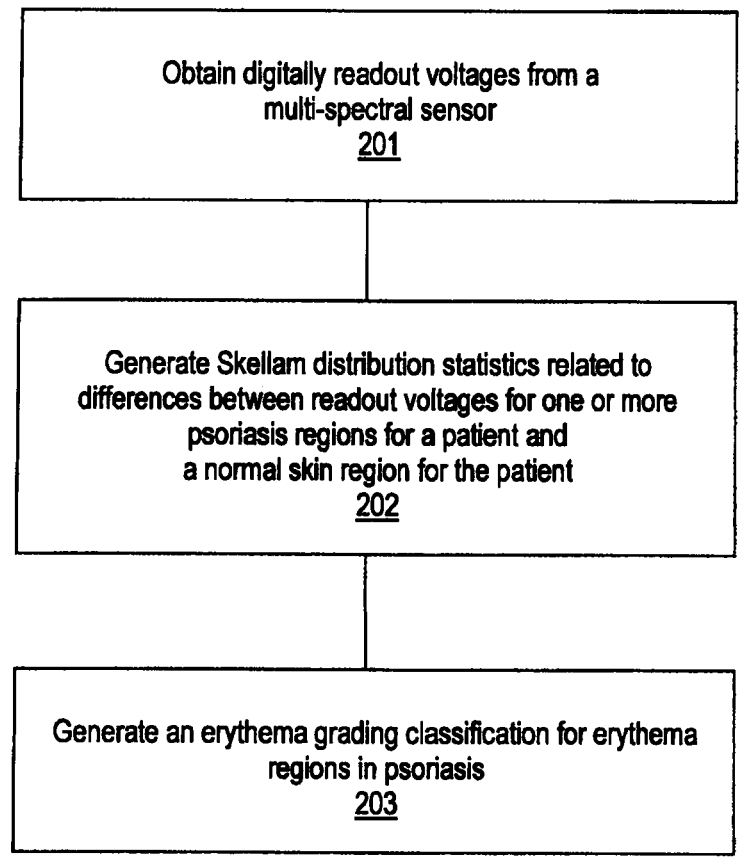
FIG. 2A is a flow diagram of one embodiment of a process for erythema grading for psoriasis.

FIG. 2A illustrates a data flow diagram of one embodiment of a process for erythema grading for psoriasis. The process is performed by processing logic that may comprise hardware (circuitry, dedicated logic, etc.), software (such as is run on a general purpose computer system or a dedicated machine), firmware, or a combination of all three.

The process begins by obtaining digitally readout voltages from a multi-spectral sensor (processing block 201). In one embodiment, each of the digitally readout voltages is a stochastically sensed value of at an induced voltage from multi-spectral digital skin images of a patient. In one embodiment, the readout voltage is indicative of image intensity for a particular wavelength in a skin region of the patient.

In response to obtaining the readout voltages, processing logic generates Skellam distribution statistics related to differences between readout voltages for one or more psoriasis regions for a patient and a normal skin region for the patient (processing block 202). In one embodiment, the Skellam distribution statistics comprise an estimate for the skin tone independent tissue photon characteristics at different scales. In one embodiment, the estimate is an estimate for a true mean.

Figure 2B:
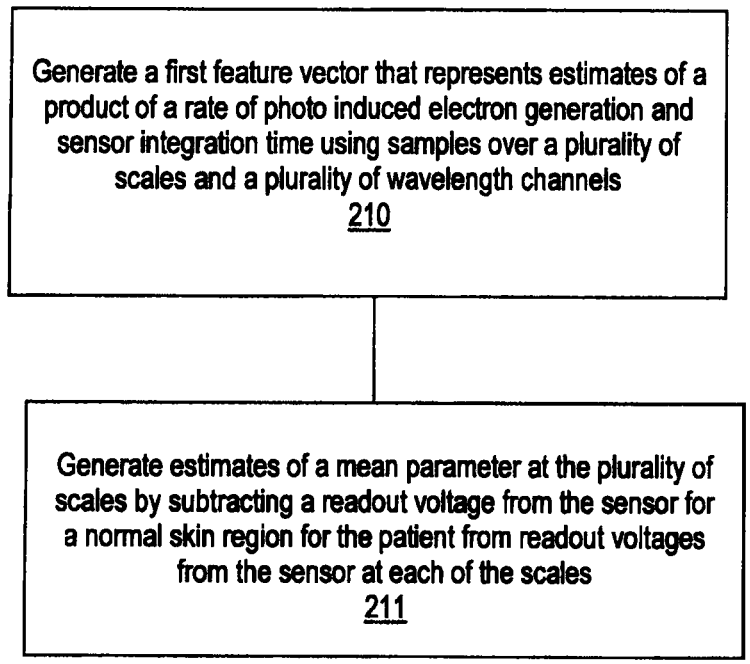
FIG. 2B is a flow diagram of one embodiment for generating Skellam distribution statistics.

FIG. 2B is a flow diagram of one embodiment for generating Skellam distribution statistics. The process is performed by processing logic that may comprise hardware (circuitry, dedicated logic, etc.), software (such as is run on a general purpose computer system or a dedicated machine), firmware, or a combination of all three.

Referring to FIG. 2B, the process begins with processing logic generating a first feature vector that represents estimates of a product of a rate of photo induced electron generation and sensor integration time using samples over a plurality of scales and a plurality of wavelength channels, wherein each scale represents a pixel region of predetermined size (processing block 210). Then processing logic generates estimates of a mean parameter at a plurality of scales by subtracting a readout voltage from a sensor for a normal skin region for the patient from readout voltages from the sensor at each of the plurality of scales (processing block 211).

Referring back to FIG. 2A, using the Skellam distribution statistics as feature vectors, processing logic generates an erythema grading classification for erythema regions in psoriasis (processing block 203). In one embodiment, generating an erythema grading classification comprises applying a random forest based operation on the feature vectors. In one embodiment, the erythema grading classification is one of multiple categories that include severe, moderate and slight.

An Embodiment of a Classifier

Figure 3:
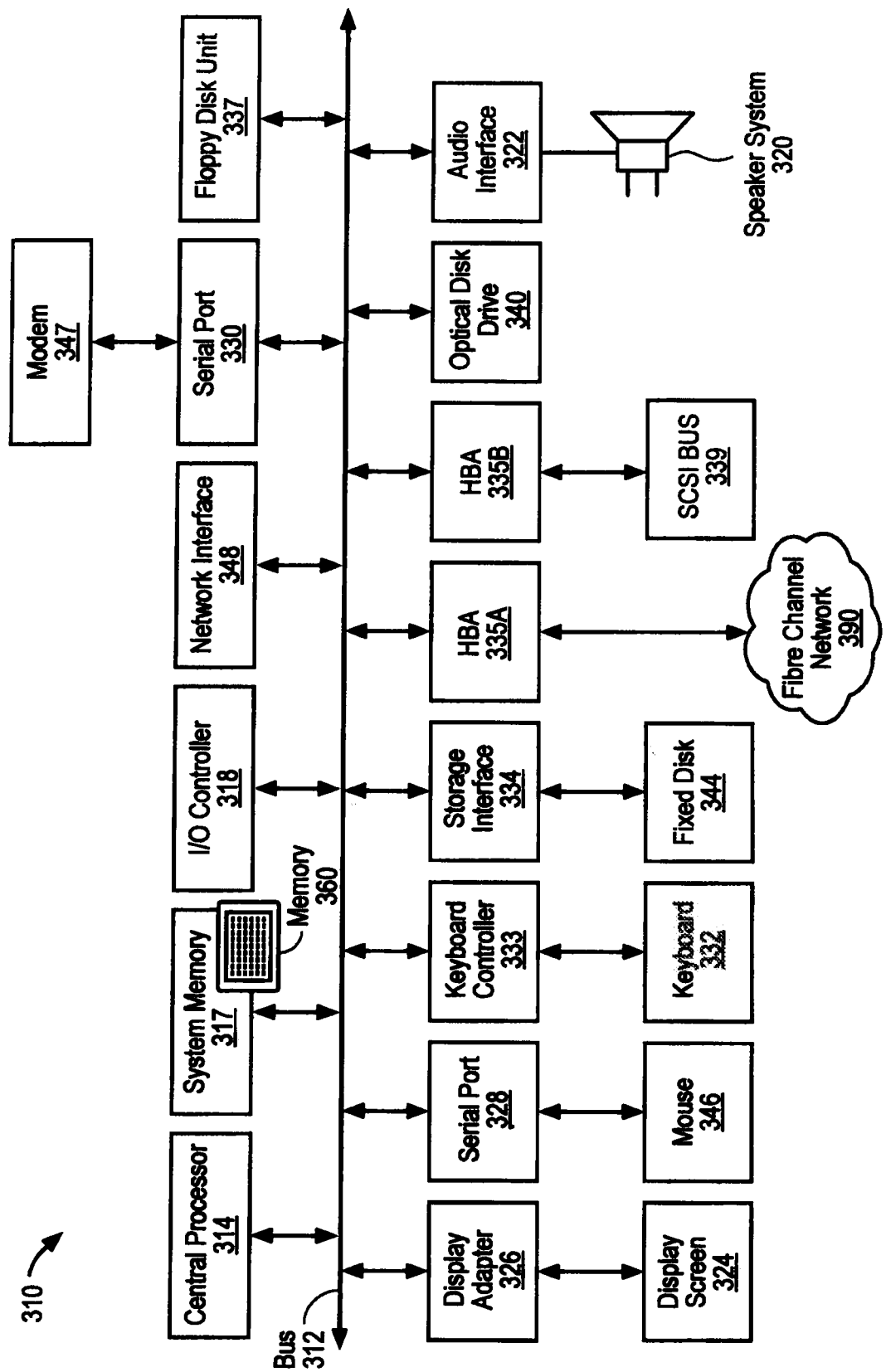
FIG. 3 depicts a block diagram of one embodiment of a computer system.

FIG. 3 depicts a block diagram of a classifier, such as classifier 102 of FIG. 1. Referring to FIG. 3, security gateway 310 includes a bus 312 to interconnect subsystems of security gateway 310, such as a processor 314, a system memory 317 (e.g., RAM, ROM, etc.), an input/output controller 318, an external device, such as a display screen 324 via display adapter 326, serial ports 328 and 330, a keyboard 332 (interfaced with a keyboard controller 333), a storage interface 334, a floppy disk drive 337 operative to receive a floppy disk 338, a host bus adapter (HBA) interface card 335A operative to connect with a Fibre Channel network 390, a host bus adapter (HBA) interface card 335B operative to connect to a SCSI bus 339, and an optical disk drive 340. Also included are a mouse 346 (or other point-and-click device, coupled to bus 312 via serial port 328), a modem 347 (coupled to bus 312 via serial port 330), and a network interface 348 (coupled directly to bus 312).

Bus 312 allows data communication between central processor 314 and system memory 317. System memory 317 (e.g., RAM) may be generally the main memory into which the operating system and application programs are loaded. The ROM or flash memory can contain, among other code, the Basic Input-Output system (BIOS) which controls basic hardware operation such as the interaction with peripheral components. Applications resident with computer system 310 are generally stored on and accessed via a computer readable medium, such as a hard disk drive (e.g., fixed disk 344), an optical drive (e.g., optical drive 340), a floppy disk unit 337, or other storage medium.

Storage interface 334, as with the other storage interfaces of computer system 310, can connect to a standard computer readable medium for storage and/or retrieval of information, such as a fixed disk drive 344. Fixed disk drive 344 may be a part of computer system 310 or may be separate and accessed through other interface systems.

Modem 347 may provide a direct connection to a remote server via a telephone link or to the Internet via an internet service provider (ISP). Network interface 348 may provide a direct connection to a remote server. Network interface 348 may provide a direct connection to a remote server via a direct network link to the Internet via a POP (point of presence). Network interface 348 may provide such a connection using wireless techniques, including digital cellular telephone connection, a packet connection, digital satellite data connection or the like. The remote server may be used to perform one or more of the operations described above.

Many other devices or subsystems (not shown) may be connected in a similar manner (e.g., document scanners, digital cameras and so on). Conversely, all of the devices shown in FIG. 3 need not be present to practice the techniques described herein. The devices and subsystems can be interconnected in different ways from that shown in FIG. 3. The operation of a computer system such as that shown in FIG. 3 is readily known in the art and is not discussed in detail in this application.

Code to implement the classifier operations described herein can be stored in a non-transitory computer-readable storage media such as one or more of system memory 317, fixed disk 344, optical disk 342, or floppy disk 338. The operating system provided on computer system 310 may be MS-DOS®, MS-WINDOWS®, OS/2®, UNIX®, Linux®, or another known operating system.

Figure 4:
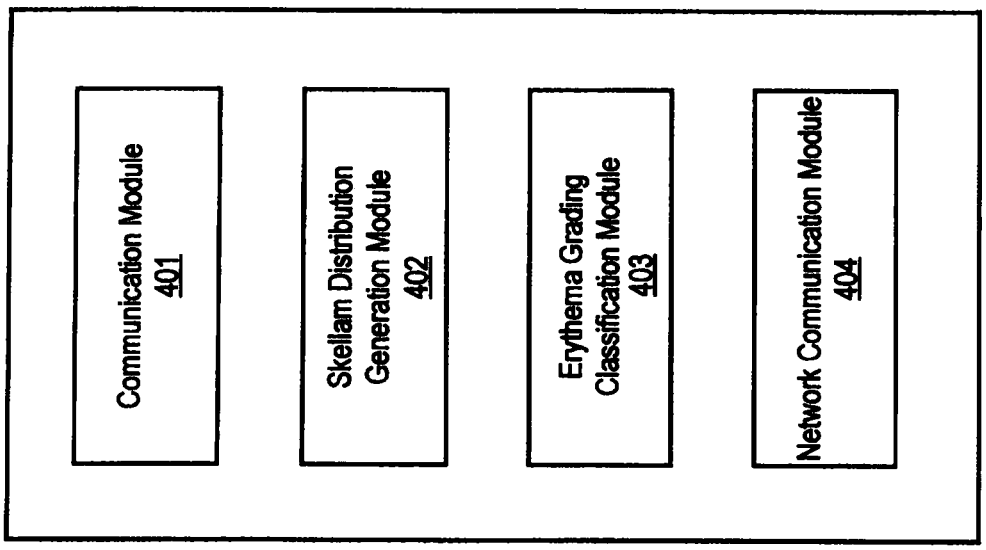
FIG. 4 illustrates a set of code (e.g., programs) and data that is stored in memory of one embodiment of the computer system.

FIG. 4 illustrates a set of code (e.g., programs) and data that is stored in memory of one embodiment of a classifier, such as classifier 101 set forth in FIG. 1. The classifier uses the code, in conjunction with a processor, to implement the necessary operations (e.g., logic operations) to implement the described herein.

Referring to FIG. 4, the memory stores a communication module 401 which when executed by a processor is responsible for receiving readout voltages from a sensor (e.g., a multi-spectral sensor, camera photo-sensor, etc.). The memory also stores a Skellam distribution statistics generation module 402 which, when executed by a processor, is responsible for generating Skellam distribution statistics. The memory also stores an erythema grading classification module 403 which, when executed by a processor, is responsible for generating an erythema grading. In one embodiment, erythema grading classification module 403 generates a classification (e.g., severe, moderate and slight) as an output by applying a random forests operation to Skellam distribution statistics. The memory also stores a network communication module 404 used for performing network communication and communication with the other devices (e.g., servers, clients, etc.).

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

I claim:

1. A method for erythema grading for psoriasis, the method comprising:

obtaining, using a processor of a system, voltages for one or more psoriasis regions on a patient and a normal skin region on the patient that are digitally read out from a multi-spectral sensor; sensor;

generating, using the processor of the system, Skellam distribution statistics related to differences between the readout voltages for the one or more psoriasis regions on the patient and the normal skin region on the patient;

generating, using the processor of the system, an erythema grading classification for the one or more psoriasis regions on the patient using a non-parametric learning algorithm that uses the Skellam distribution statistics as feature vectors for the erythema grading classification, wherein the erythema grading classification is one of multiple categories that include severe, moderate and slight; and displaying, using the processor, a classification result associated with the erythema grading classification on a display.

2. The method defined in claim 1 wherein each of the digitally readout voltages is a stochastically sensed value of an induced voltage from multi-spectral digital skin images of the patient.

3. The method defined in claim 1 wherein the Skellam distribution statistics comprise an estimate for skin tone independent tissue photon characteristics at different scales.

4. The method defined in claim 3 wherein the estimate is an estimate for a true mean.

5. The method defined in claim 1 further comprising:
generating a first feature vector that represents estimates of a product of a rate of photo induced electron generation and sensor integration time using samples over a plurality of scales and a plurality of wavelength channels, wherein each scale represents a pixel region of predetermined size; and
generating estimates of a mean parameter at a plurality of scales by subtracting a readout voltage from a sensor for a normal skin region for the patient from readout voltages from the sensor at each of the plurality of scales.

6. The method defined in claim 5 wherein the readout voltage is indicative of image intensity for a particular wavelength for a skin region of the patient.

7. The method defined in claim 1 wherein the non-parametric learning algorithm comprises a random forest algorithm, and wherein generating the erythema grading classification comprises applying the random forest based operation on the feature vectors.

8. A non-transitory computer readable storage medium that stores instructions, which when executed on a classification system, causes the system to perform a method comprising:
obtaining voltages for one or more psoriasis regions on a patient and a normal skin region on the patient that are digitally read out from a multi-spectral sensor;
generating, using a processor of a system, Skellam distribution statistics related to differences between the readout voltages for the one or more psoriasis regions on the patient and the normal skin region on the patient;
generating, using a processor of a system, an erythema grading classification for the one or more psoriasis regions on the patient using a non-parametric learning algorithm that uses the Skellam distribution statistics as feature vectors for the erythema grading classification, wherein the erythema grading classification is one of multiple categories that include sever, moderate and slight; and
displaying a classification result associated with the erythema grading classification on a display.

9. The computer readable storage medium defined in claim 8 wherein each of the digitally readout voltages is a stochastically sensed value of an induced voltage from multi-spectral digital skin images of the patient.

10. The computer readable storage medium defined in claim 8 wherein the Skellam distribution statistics comprise an estimate for skin tone independent tissue photon characteristics at different scales.

11. The computer readable storage medium defined in claim 10 wherein the estimate is an estimate for a true mean.

12. The computer readable storage medium defined in claim 8 wherein the method further comprising:
generating a first feature vector that represents estimates of a product of a rate of photo induced electron generation and sensor integration time using samples over a plurality of scales and a plurality of wavelength channels, wherein each scale represents a pixel region of predetermined size;
generating estimates of a mean parameter at a plurality of scales by subtracting a readout voltage from a sensor for a normal skin region for the patient from readout voltages from the sensor to create a difference at each of the plurality of scales; and
distributing the differences as a Skellam distribution for each scale of the plurality of scales.

13. The computer readable storage medium defined in claim 12 wherein the readout voltage is indicative of image intensity for a particular wavelength for a skin region of the patient.

14. The computer readable storage medium defined in claim 8 wherein the non-parametric learning algorithm comprises a random forest algorithm, and wherein generating the erythema grading classification comprises applying the random forest based operation on the feature vectors.

15. A system comprising:
a processor;
one or more sensors coupled to the processor to generate readout voltages indicative of image intensity for a particular wavelength for one or more psoriasis regions on a patient and a normal skin region on the patient; and
a classifier coupled the processor to receive the readout voltages from the one or more sensors to perform erythema grading for psoriasis, the classifier coupled to the processor, in response to the readout voltages, to generate Skellam distribution statistics related to differences between the readout voltages for the one or more psoriasis regions on the patient and the normal skin region on the patient and to generate an erythema grading classification for the one or more psoriasis regions on the patient using a non-parametric learning algorithm that uses the Skellam distribution statistics as feature vectors for the erythema grading classification, wherein the erythema grading classification is one of multiple categories that include sever, moderate and slight; and
a hardware coupled to the processor to display a classification result associated with the erythema grading classification.

16. The system defined in claim 15 wherein the one or more sensors obtains voltages digitally read out, wherein each of the digitally readout voltages is a stochastically sensed value of an induced voltage from multi-spectral digital skin images of a patient.

17. The system defined in claim 15 wherein the Skellam distribution statistics comprise an estimate for skin tone independent tissue photon characteristics at different scales.

18. The system defined in claim 15 wherein the non-parametric learning algorithm comprises a random forest algorithm and wherein the classifier generates the erythema grading classification by applying the random forest based operation on the feature vectors.

\* \* \* \* \*